United States Patent [19]

Siposs

[11] Patent Number: 4,642,097
[45] Date of Patent: Feb. 10, 1987

[54] LEFT VENTRICAL VACUUM CONTROL AND PRESSURE RELIEF VALVE

[76] Inventor: George G. Siposs, 2855 Velasco La., Costa Mesa, Calif. 92626

[21] Appl. No.: 715,928

[22] Filed: Mar. 25, 1985

[51] Int. Cl.⁴ ............................................ F16K 17/164
[52] U.S. Cl. ........................................ 604/119; 604/118; 604/119; 604/32; 604/129; 604/248; 137/512.3; 15/421; 251/345
[58] Field of Search ................. 604/119, 9, 32, 33, 604/35, 118, 128, 129, 236, 247, 248; 137/512.3, 606; 251/342, 345; 15/339, 415, 421; 128/207.16, 207.17

[56] References Cited

U.S. PATENT DOCUMENTS

| | | | |
|---|---|---|---|
| 2,176,139 | 10/1939 | Lofgren | 604/119 |
| 3,039,463 | 6/1962 | Dickey, Jr. et al. | 15/421 |
| 3,395,705 | 8/1968 | Hamilton | 604/119 |
| 3,942,596 | 3/1976 | Millsapps, Jr. | 137/512.3 |
| 3,958,566 | 5/1976 | Furihata | 604/35 |
| 3,998,227 | 12/1976 | Holbrook et al. | 604/119 |
| 4,502,502 | 3/1985 | Krug | 604/118 |
| 4,512,765 | 4/1985 | Muto | 604/119 |
| 4,543,101 | 9/1985 | Crouch | 604/411 |

FOREIGN PATENT DOCUMENTS 2315285  1/1977  Fed. Rep. of Germany ...... 604/119

Primary Examiner—C. Fred Rosenbaum
Assistant Examiner—Mark Rooney
Attorney, Agent, or Firm—Allen A. Dicke, Jr.

[57] ABSTRACT

The valve is positioned in the left ventricle drain line and includes a check valve which permits flow only away from the heart and downstream of the check valve includes a vent valve which prevents buildup of pressure. In addition, the valve includes a manually adjustable vacuum control orifice whereby the surgeon can control the left ventricle drain line vacuum intensity applied to the heart.

19 Claims, 4 Drawing Figures

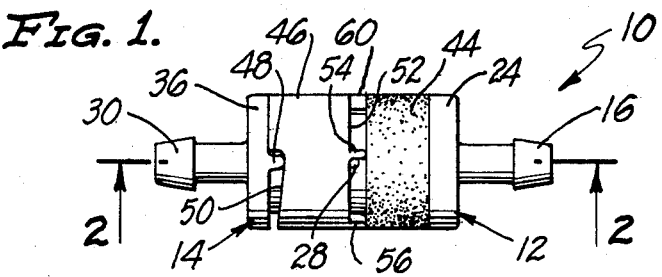
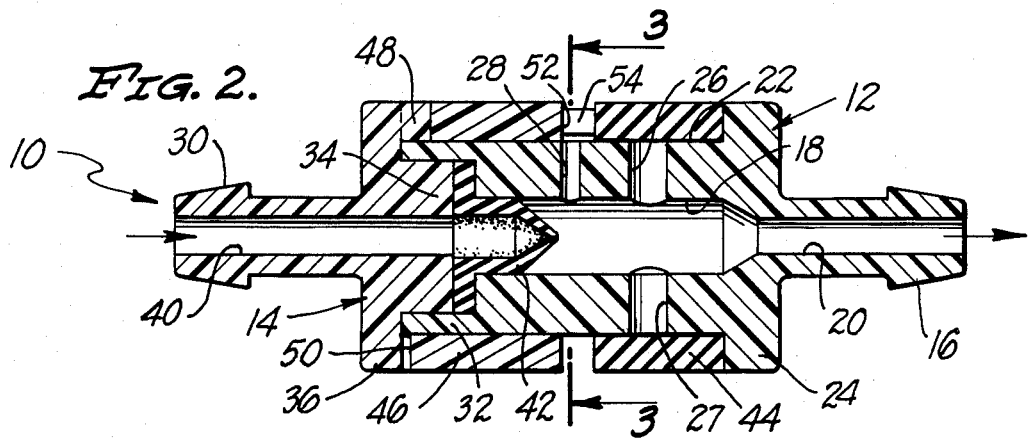
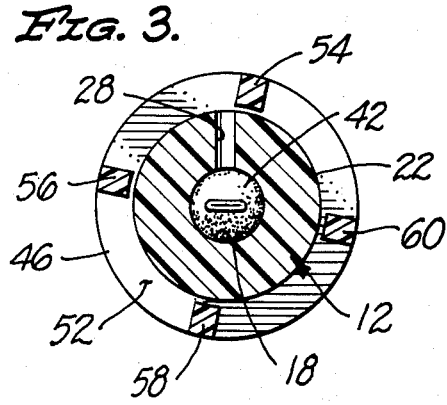
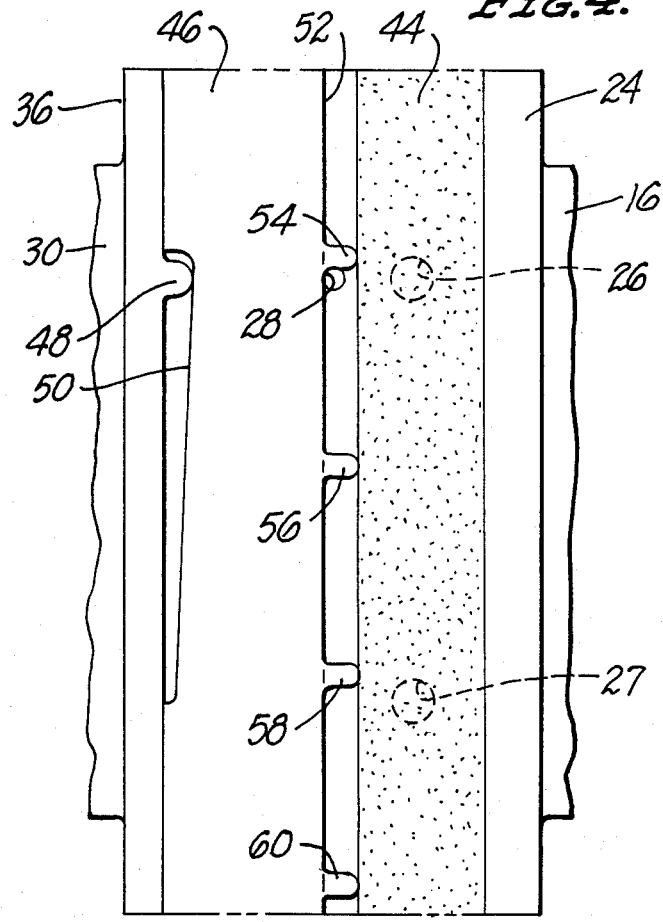

LEFT VENTRICAL VACUUM CONTROL AND PRESSURE RELIEF VALVE

BACKGROUND OF THE INVENTION

This invention is directed to a valve which controls the vacuum applied to the left ventricle during open-heart operation, prevents reverse flow to the heart, and vents the line of gas or blood should pressure rise above atmosphere.

During some open-heart procedures, even though the heart is bypassed with the open-heart tubing, some blood finds its way into the left ventricle of the heart. Unless the blood is drained from the left ventricle, the blood causes the heart to distend. Such distension makes it difficult or impossible to resuscitate the heart at the end of the procedure. For this reason, some surgeons attach a slender tubing to the left ventricle to drain the blood from it. A suction pump may be used to provide the vacuum to remove the blood. Several problems may be caused by such a method. One problem arises if the opening of the drain line tube attaches itself to the inside of the heart chamber. This causes suction to be stopped, and the tubing must be wrenched away from the tissue. This causes trauma to the chamber tissue. The valve enables the surgeon to regulate the suction intensity to the desired level so that it is easier to pull the tube away from tissue. It has been found in clinical trials that 150 mm Hg is a good compromise between suction and adhesion to tissue.

Another problem which may occur during left heart venting arises from the fact that the amount of suction to the heart through the left ventricle drain line is regulated by the speed of the vacuum pump. The vacuum pump is controlled by the heart-lung machine technician so that the surgeon must communicate to the technician the amount of suction desired. Many times, suction intensity is either too great or too little.

Another problem which may occur in such an organization is the buildup of pressure in the left ventricle drain line. This would drive air into the heart and cause an air embolism and even possible death of the patient. Such inadvertent pressure in the left ventricle drain line could be caused by any one of several means. For example, the vacuum pump switch could accidentally be positioned to run the pump in reverse so that instead of suction, pressure would be produced in the drain line. Another possible cause of such pressure would occur when the suction pump is connected to discharge into a closed reservoir in which the pump causes a pressure buildup. In such a case, there is a chance that when the pump is stopped, the pressure may leak back through the drain line into the heart. Another cause of pressure buildup in the drain line is in the structure of the roller pump. In a roller pump, the tubing may be accidentally inserted in a backward orientation into the pump housing so that even if the pump switch is in the "Forward" position, the pump is working backward.

In order to prevent such problems from causing dangers to the patient, the present left ventricle vacuum control and pressure relief valve was created. This valve enables the surgeon to personally set the suction level at the operating table instead of at the pump, which he cannot conveniently reach. In this case, the pump can be left running at one speed, and the surgeon can adjust the suction pressure at his convenience. In addition, this valve prevents flow toward the heart and allows flow only away from the heart, whether the flow be blood or air. Furthermore, the valve of this invention permits any pressure in the downstream line to be vented to the atmosphere instead of being transmitted to the heart. When the venting is accompanied by the escape of blood from the valve, the surgeon is immediately notified that something is wrong (for example, there is inadequate suction to remove the blood) and can take corrective measures.

SUMMARY OF THE INVENTION

In order to aid in the understanding of this invention, it can be stated in essentially summary form that it is directed to a left ventricle vacuum control and pressure relief valve which includes a body having a passage therethrough and a check valve therein which permits flow only from the inlet toward the outlet. Downstream of the check valve is a vent valve and an opening with manually adjustable flow area to control the amount of vacuum downstream of the check valve by allowing air to bleed into the passage.

It is, thus, an object and advantage of this invention to provide a valve for the left ventricle drain line which permits flow only away from the heart.

It is another purpose and advantage of this invention to provide a valve for the left ventricle drain line which permits manual control of the vacuum applied to the heart while the suction pump runs at a constant speed.

It is a further object and advantage of this invention to provide a valve for the left ventricle drain line which automatically vents pressure in excess of atmospheric pressure to prevent pressure buildup toward the heart, to vent blood if suction is inadequate, and to vent air if pressure builds up in the outlet end of the drain line.

It is a further object and advantage of this invention to provide a valve for the left ventricle drain line which is simple, can be positioned close to the surgeon, can be manually operated, and can be accurately mass-produced and pre-sterilized so that it can be easily and safely inserted in the left ventricle drain line.

Other objects and advantages of this invention will become apparent from a study of the following portion of the specification, the claims and the attached drawings.

BRIEF DESCRIPTION OF THE DRAWINGS

FIG. 1 is a side-elevational view of the valve in accordance with this invention.

FIG. 2 is an enlarged section taken generally along the line 2—2 of FIG. 1.

FIG. 3 is a transverse section taken generally along the line 3—3 of FIG. 2.

FIG. 4 is a projected view of the exterior of the valve, on the scale seen in FIG. 2.

DESCRIPTION OF THE PREFERRED EMBODIMENT

The left ventricle vacuum control and pressure relief valve of this invention is generally indicated at 10 in FIGS. 1, 2 and 3. Valve 10 is shown in longitudinal section in FIG. 2 and is shown in transverse section in FIG. 3. Valve 10 has a body 12 and an inlet fitting 14. Body 12 has an outlet barbed nipple 16 on its outlet end with the nipple sized to be received in the left ventricle drain line. Passage 18 in the body adjoins passage 20 in the nipple, with the passages extending end-to-end through the body, defining a central axis therethrough.

Body 12 has an external surface 22 which is cylindrical about the axis. Shoulder 24 extends radially outward at the right end of the body. Relief passages 26 and 27 are radial passages of circular cross section which extend from the internal passage 18 to the external surface 22. Vacuum control passage 28 also is a radially oriented passage of circular cross section extending from the internal passage 18 to the external surface 22.

Cap 14 has a barbed inlet nipple 30 thereon sized the same as nipple 16 so that the left ventrical drain line can be cut at an appropriate location and the valve 10 inserted therein, with the valve connected to both ends of the line. Body 12 has a circular flange 32 extending to the left therefrom, as seen in FIG. 2, which embraces around a rightward extending circular extension 34 of the cap 14. These interengaging portions provide alignment for the cap on the body and provide for securement of the cap on the body, as by adhesive means, heat sealing, or preferably by ultrasonic joining. Cap 14 has shoulder 36 thereon which corresponds to shoulder 24.

Inlet nipple 30 and cap 14 also have passage 40 therein which is in alignment with passages 18 and 20. Valve 42 is structured so that it permits flow from left to right through valve 10, as seen in FIG. 2, into the inlet ipple 30 and out of outlet nipple 16. The valve 42 is an elastomeric molding of generally cylindrical configuration, but, as seen in FIG. 3, has a pair of flat lips which lie together. These are conventionally molded in one piece and slit afterwards. The result is a valve which opens to flow in the left-to-right direction with very low differential pressure and lies closed essentially without a differential pressure. If the pressure is higher on the right side, as seen in FIG. 2, the valve lips are forced closed to inhibit flow. Such valves are often called "duckbill" valves from their physical resemblance. Thus, valve 42 is a check valve which permits flow only in the left-to-right direction through valve 10. Passage 40 aligns with the interior opening within valve 42, while passage 18 embraces the main body of valve 42. An outwardly directed flange is captured between extension 32 on the body 12 and extension 34 on cap 14.

Elastic ring 44 is engaged around external surface 22 and lies against shoulder 24. Elastic ring 44 is a cylindrical tube which gently engages upon surface 22. When the pressure rises in the central chamber of valve 10, in passage 18, the pressure in relief passages 26 and 27 lifts elastic ring 44 to permit venting of the pressure. Pressure also vents through hole 28. However, when there is vacuum in passage 18, elastic ring overlies the opening of relief passage 26 to prevent inflow from atmosphere, except through hole 28. Thus, elastic ring 44 serves as the auxiliary active member in the pressure relief function of valve 10.

Sleeve 46 is a substantially rigid sleeve generally in the form of a cylindrical tube which lies on and is rotatable/slidable with respect to surface 22. Sleeve 46 is an adjustment sleeve and is rotatable on surface 38 on the exterior of the valve body. Cam stop 48 is formed on shoulder 36 and faces spirally shaped cam ramp surface 50 on sleeve 46. As the sleeve 46 is rotated in the direction shown in FIG. 3, from the position of FIG. 1 for approximately 180 degrees, the sleeve 46 is forced to the right by the ramp surface 50 rising up cam stop 48. In the beginning position shown in FIGS. 1 and 2, the right-hand end surfaces 52 of sleeve 46 is in alignment with the left edge of vacuum control passage 28. As the sleeve is rotated from the end position of FIG. 1 where the control passage 28 is opened to its other end position, the vacuum control passage 28 is slowly closed. When the vacuum control passage 28 is full open, then the minimum vacuum is applied to passage 40, but when the passage 28 is fully closed by rotation of sleeve 46, a higher vacuum intensity is applied to the passage 40. At intermediate positions of sleeve 46, the vacuum in passage 40 is controlled to levels between these minimum and maximum levels.

Elastic ring 46 performs two functions with respect to sleeve 46. Projections 54, 56, 58 and 60 are formed on the sleeve and extend to the right to engage against elastic ring 44, as seen in FIGS. 1, 2 and 4. Engagement of these projections against the elastic ring creates rotational friction so that when left alone, the ring 46 will maintain its position. Also, ring 44 exerts axial pressure against ring 46 to prevent inadvertent closure of passage 28 by slippage of the sleeve 46 to the right. In this way, elastic ring 44 acts to resiliently hold the ramp surface 50 against cam stop 48 to maintain accurate correspondence between angular rotation of sleeve 46 with respect to opening of the control passage 28.

Elastic ring 44 also serves to prevent inadvertent rotation of adjustment sleeve 46. The projections 54 through 60 dig into the elastic ring 44 to resist such rotation. The indentations of the projections into the elastic ring prevent rotation. Therefore, the adjustment sleeve 46 can be turned to the desired location, but will remain there until the sleeve 46 is again grasped and rotated. Projections 54 through 60 do not lie against the external surface 22, as is seen in FIGS. 2 and 3, in order to prevent the projections from interfering with the amount of opening of the vacuum control passage 28.

As an economic and satisfactory method of manufacture, the body 12, cap 14 and sleeve 46 can be injection-molded of fairly rigid thermoplastic synthetic polymer composition bicompatible material. Valve 42 is injection-molded of an elastomer, and after the molding, the valve opening is cut with a razor or the like. Elastic ring 44 can be sliced from an extruded tube or can be molded from thermoplastic elastomer. After the assembly of the parts into the organization shown in FIG. 2, the structure is permanently assembled by attachment between flange 32 and extension 34, by adhesive means for example. All of the parts must be of suitable characteristics for sterilization.

In the preferred utilization, the valve 10 is placed in the left ventricle vent line about 2 feet from and level with the heart so that the valve is positioned ear the patient's groin on the sterile drape within easy reach of the surgeon. The amount of suction desired in most cases is about 160 mmHg. The pump speed is adjusted so that this level of vacuum is reached when the vacuum control passage 28 is about half covered by vacuum adjustment sleeve 46. During the operation, the surgeon can readily alter the vacuum intensity. Should the suction pump not be operating or should the suction pump be operating too slowly and the heart is putting blood into the left ventricle drain line, blood in the valve will leak out of the valve through relief passage 28 and vacuum control passage 28. This presence of blood will immediately warn the surgeon of an undersirable condition. Efforts can be made to increase to suction to withdraw the blood from the left ventricle drain line. In this manner, the blood is safely drained from the left ventricle, with the level of vacuum being controlled by the surgeon. The valve incorporates structure which permits the relief of pressure and incorporates structure which prevents the reverse flow of fluid through the left ventricle drain line and, accordingly, the requirements of the application are satisfied.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A valve for the control of vacuum in the left ventricle drain line, said valve comprising:
    a valve body connectible in the left ventricle drain line between a patient and a suction pump, said body having a flow passage therethrough having an inlet end and an outlet end, a vacuum control passage in said body extending from said passage through said body to the atmosphere;
    a rotatable sleeve positioned on the exterior of said body valve to rotate on said valve body with respect to said vacuum control passage to variably cover said vacuum control passage to control the effective area of said vacuum control passage so as to control inflow through said vacuum control passage from the atmosphere into said flow passage through said body whereby vacuum can be controlled within said flow passage;
    walls defining a relief passage in said body extending from said flow passage to the exterior of said body; and
    a tubular elastomeric member on said body covering said relief passage so that when pressure in said flow passage is below external pressure said relief passage is closed and when pressure in said flow passage is above external pressure, fluid in said flow passage discharges out of said relief passage out from under said tubular elastomeric member, said rotatable sleeve being in resilient contact with said elastomeric member to provide rotational friction for said rotatable sleeve so that it stays in place where set.

2. The valve of claim 1 wherein said movable member is positioned so that said movable member can be manually grasped for movement of said movable member to control opening of said vacuum control passage.

3. The valve of claim 2 wherein said rotatable sleeve has an angular surface thereon so that as said sleeve is rotated on said body the opening of said vacuum control passage is changed.

4. The valve of claim 3 further including a check valve within said body for limiting flow through said passage through said body from an inlet end of said body to an outlet end of said body.

5. The valve of claim 4 wherein said vacuum control passage is positioned between said check valve and said outlet from said body.

6. The valve of claim 5 wherein said check valve is a duckbill valve.

7. The valve of claim 1 further including a check valve within said body for limiting flow through said passage through said body from an inlet end of said body to an outlet end of said body.

8. The valve of claim 7 wherein said vacuum control passage is positioned between said check valve and said outlet from said body.

9. The valve of claim 8 wherein said check valve is a duckbill valve.

10. A valve comprising:
    a valve body, an inlet connection and an outlet connection on said valve body for connection in a left ventricle drain line between a patient and a suction pump, a passage through said valve from said inlet to said outlet;
    a vacuum control passage in said body from said through passage to the exterior of said body;
    a movable part on said body, said movable part being positioned for manual engagement and being movable from a position where it substantially covers said vacuum control passage to a position where it substantially uncovers said vacuum control passage so that vacuum in said passage through said body can be controlled by movement of said part;
    walls defining a relief passage in said valve body extending from said passage to the exterior of said body; and
    an elastomeric member on said body covering said relief passage so that when pressure in said passage is below external pressure said relief passage is closed and when pressure in said flow passage is above external pressure, fluid in said passage discharges out of said relief passage out from under said elastomeric member, said movable part being in resilient contact with said elastomeric member to provide friction for said movable part so that it stays in place where set.

11. The valve of claim 10 wherein said body has a substantially cylindrical surface thereon and said part is a sleeve rotatable on said substantially cylindrical surface, said sleeve having an angular ramp surface thereon so that as said sleeve is rotated on said body said ramp surface causes a progressive uncovering of said vacuum control passage.

12. The valve of claim 11 wherein said elastomeric member engages said sleeve to urge said sleeve in a direction on said body in a direction away from said vacuum control passage.

13. The valve of claim 12 wherein there is a shoulder on said body and a cam stop on said shoulder, said angular ramp surface on said sleeve being in engagement with said cam stop so that rotation of said sleeve on said body causes axial motion of said sleeve on said body with motion in a direction to cover said vacuum control passage being motioned toward said elastomeric member.

14. A valve comprising:
    a valve body, an inlet connection and an outlet connection on said valve body for connection in a left ventricle drain line between a patient and a suction pump, a passage through said valve from said inlet to said outlet, said body having a substantially cylindrical surface thereon and a shoulder on said body adjacent said cylindrical surface together with a cam stop on said shoulder;
    a vacuum control passage in said body from said passage to the exterior of said body on the substantially cylindrical surface of said body;
    a relief passage in said body from said passage through said body to the exterior of said body through the substantially cylindrical surface of said body;
    a sleeve rotatably mounted on said body on said substantially cylindrical surface, said sleeve having an angular ramp surface thereon so that as said sleeve is rotated on said body said ramp surface causes a progressive uncovering of said vacuum control passage, said angular ramp surface on said sleeve being in engagement with said cam stop so that rotation of said sleeve on said body causes axial motion of said sleeve on said body for the progressive uncovering of said vacuum control passage;

an elastomeric member on said body, said elastomeric member being in engagement with said sleeve to urge said sleeve in a direction on said body away from said vacuum control passage, said relief passage in said body being underneath said elastomeric member so that said elastomeric member also acts to vent pressure from the passage through said body to the exterior of said body.

15. The valve of claim 14 wherein said elastomeric member is a ring embracing said body.

16. A valve comprising:

a valve body, an inlet connection and an outlet connection on said valve body for connection in a left ventricle drain line between a patient and a suction pump, a passage through said valve from said inlet to said outlet, said body having an exterior surface thereon;

a relief passage in said body from said passage through said body to the exterior of said body;

a vacuum control passage in said body from said passage through said body to the exterior of said body;

said body having a substantially cylindrical surface on the exterior thereof, a sleeve rotatable on said substantially cylindrical surface, said sleeve having an annular ramp surface thereon so that as said sleeve is rotated on said body said ramp surface causes a progressive uncovering of said vacuum control passage;

an elastomeric member on said body in engagement with said sleeve to elastically retain said sleeve in a selected position, said relief passage being underneath said elastomeric member so that said elastomeric member also acts to vent pressure from the passage through said body to the exterior of said body.

17. The valve of claim 16 wherein said elastomeric member is a ring embracing said body.

18. The valve of claim 17 further including a check valve within said body to limit flow through said passage through said body from said inlet to said outlet and said vacuum control passage is positioned between said check valve and said outlet.

19. The valve of claim 15 further including a check valve within said body to limit flow through said passage through said body from said inlet to said outlet and said vacuum control passage is positioned between said check valve and said outlet.

* * * * *